United States Patent [19]

Bantu et al.

[11] Patent Number: 5,281,723
[45] Date of Patent: Jan. 25, 1994

[54] PROPYLENE CARBONATE RECOVERY PROCESS

[75] Inventors: Nageshwer R. Bantu, Endicott; Anilkumar C. Bhatt, Johnson City; Ross W. Keesler, Owego; Konstantinos Papathomas, Endicott; Terry D. Sinclair, Endicott; Jerome J. Wagner, Endicott, all of N.Y.

[73] Assignee: International Business Machines, Armonk, N.Y.

[21] Appl. No.: 925,349

[22] Filed: Aug. 4, 1992

[51] Int. Cl.$^5$ .......................................... C07D 317/08
[52] U.S. Cl. .................................. 549/230; 549/228; 549/229
[58] Field of Search .................... 549/230, 228, 229

[56] References Cited

U.S. PATENT DOCUMENTS

| | | | |
|---|---|---|---|
| 2,766,258 | 10/1956 | Malkemus | 549/230 |
| 2,894,957 | 7/1959 | Anderson et al. | 549/230 |
| 3,074,962 | 1/1963 | Anderson et al. | 549/230 |

Primary Examiner—Cecilia Tsang
Attorney, Agent, or Firm—Richard M. Goldman

[57] ABSTRACT

Disclosed is a method of recovering a cyclic alkylene carbonate, such as propylene carbonate, from an effluent stream of a process in which the cyclic alkylene carbonate removes an organic photoresist material from a substrate. The effluent is a cyclic alkylene carbonate effluent, e.g., a propylene carbonate effluent, of the carbonate, water, and polymeric solids. In the recovery process the cyclic alkylene carbonate effluent is fed to a heat exchanger, and separated into (i) water and volatiles, and (ii) cyclic carbonate. This lowers the concentration of water in the cyclic alkylene carbonate to a level that is low enough to substantially avoid hydrolysis of cyclic alkylene carbonate to the corresponding glycol. The dewatered cyclic alkylene carbonate is evaporated to separate the cyclic alkylene carbonate from high boiling materials and polymeric solids. The dewatered cyclic alkylene carbonate is separated into (i) a cyclic alkylene carbonate fraction, and (ii) a photoresist solids fraction. The photoresist materials fractions contains photoresist material in the alkylene carbonate. The cyclic alkylene carbonate fraction is further separated in a fractionation means into a higher vapor pressure alkylene glycol fraction, and a lower vapor pressure alkylene carbonate fraction.

47 Claims, 4 Drawing Sheets

PROPYLENE CARBONATE RECOVERY PROCESS

CROSS REFERENCE TO RELATED APPLICATIONS

This application is related to the following commonly assigned, copending U.S. patent applications:
1. U.S. application Ser. No. 07/781,542, filed Oct. 22, 1991, of N. R. Bantu, Anilkumar Bhatt, Ashwinkumar Bhatt, G. W. Jones, J. A. Kotylo, R. J. Owen, K. I. Papathomas, and A. K. Bardya for Photoresist Develop And Strip Solvents and Methods for their Use.
2. U.S. application Ser. No. 07/924,740 filed Aug. 4, 1992, of Kevin P. Unger and James A. Shurtleff for Chemical Pre-Treatment and Biological Destruction of Propylene Carbonate Effluent Streams.

FIELD OF THE INVENTION

The invention described herein relates to environmentally compatible developers and stripping solvents for photoresist materials. Specifically, the invention relates to cyclic alkylene carbonate solvents, such as propylene carbonate, as substitutes for such chlorinated solvents as Methyl Chloroform (MCF; 1,1,1-Trichloroethane) and Methylene Chloride (MC; Dichloromethane). Impure liquid compositions of propylene carbonate and photoresist and/or solder mask material are recovered from circuit panel manufacturing processes. According to the invention described herein the impure liquid product of the manufacturing process is treated to recover the cyclic alkylene carbonate, for example, propylene carbonate.

BACKGROUND OF THE INVENTION

Photolithographic processes in packaging are described in *Microelectronics Packaging Handbook*, Pub. Van Nostrand Reinhold, New York, 1989, Tummala et al, eds. on pages 898-903, in *Principles of Electronic Packaging*, McGraw-Hill Book Company, New York, 1989, Seraphim et al, eds. in Chapter 12, pages 372-393 and in Scientific Encyclopedia, 6th Ed., Vol. II, Pub. Van Nostrand Reinhold Company, New York, 1983, Considine et al, eds., pages 1877-1881, all of which are incorporated herein by reference for use as background.

Photolithography plays a critical role in the art of printed circuit packaging. Photolithography is used to define in a thin film of photoresist those regions either from which copper is to be selectively etched to subtractively form circuitization, or selectively plated to additively form circuitization.

There are two types of photoresist: negative and positive. A negative photoresist is polymerized by exposure, e.g., selective exposure to the particular actinic radiation to which it is sensitive for an adequate period of time. It is then subjected to its developer. The developer solubilizes the areas of the resist which have not been exposed to actinic radiation. The areas of negative photoresist which have been exposed to actinic radiation are hardened by cross-linking and made more resistant to developer, relative to the unexposed regions.

Positive acting resists behave oppositely. Actinic radiation renders the positive acting photoresist more soluble in the developer, and the exposed regions are removed preferentially by a dilute alkaline developer.

Positive acting photoresists are used extensively to fabricate silicon devices, and for subtractive circuitization of printed circuit boards. However, positive photoresists, which are readily developed by dilute aqueous alkaline solutions and stripped by more concentrated aqueous alkaline solutions, perform poorly in high caustic environments and high temperatures.

The negative resists, on the other hand, are used when the circuit lines are provided by additive plating of copper, in areas where copper is desired, i.e., electroless or electroless plus electroplating, rather than by etching of copper away from where it is not desired.

Negative acting photoresists are cross-linked by the action of actinic energy on photoactive agents that form the free radicals or ionic groups necessary to initiate and/or support polymerization. Depending on their composition, commercially available photoresists are sensitive to UV radiation, X-rays, E-beams and so forth. The radiation may be furnished to the resist through a pattern in a mask, such as an emulsion mask or chrome mask, by contact or projection, or a beam of radiation may be rastered.

Negative acting photoresists include an organic resin binder, a photoinitiator/photosensitizer and a reactive monomer. Optionally, negative acting photo-resists also include fillers, for example, organic or inorganic fillers, fire retardants, plasticizers, dyes, flexibilizers, thermal stabilizers and other additives to improve the processing characteristics of the package.

Typical negative photoresist compositions include from 40 to 70% by weight of binder, 10 to 40% by weight of monomer, and 0.5 to 15% by weight of photoinitiator, to total 100% based on the weight of all these components.

An example of such compositions is described in U.S. Pat. No. 4,326,010. (example 1).

In general, negative-working resists are photopolymerizable materials of the type described in U.S. Pat. Nos. 3,469,982, 4,273,857 and U.S. Pat. No. 4,293,635 and the photocrosslinkable species of the type disclosed in U.S. Pat. No. 3,526,504.

Monomers which can be used either alone or in combination with others to form negative acting photoresists include: t-butyl acrylate, 1,5 pentanediol diacrylate, N,N-diethylaminoethyl acrylate, ethylene glycol diacrylate, 1,4-butanediol diacrylate, diethylene glycol diacrylate, hexamethylene glycol diacrylate, 1,3-propanediol diacrylate, decamethylene glycol diacrylate, decamethylene glycol dimethacrylate, 1,4-cyclohexanediol diacrylate, 2,2-dimethylolpropane diacrylate, glycerol diacrylate, tripropylene glycol diacrylate, glycerol triacrylate, trimethylolpropane triacrylate, pentaerythritol triacrylate, polyoxyethylated trimethylolpropane triacrylate and trimethacrylate and similar compounds as disclosed in U.S. Pat. No. 3,380,831, 2,2-di-(p-hydroxyphenyl)-propane diacrylate, pentaerythritol tetraacrylate, 2,2-di(p-hydrohyphenyl)-propane dimethacrylate, triethylene glycol diacrylate, polyoxyethyl-2,2-di-( p-hydroxyphenyl)-propane dimethacrylate, di-(3-methacryloxy-2-hydroxypropyl) ether of bisphenol-A, di-(2-methacryloxyethyl) ether of bisphenol-A, di-(3-acryloxy-2-hydroxypropyl) ether of bisphenol-A, di-(2-acryloxyethyl) ether of bisphenol-A, di-(3-methacryloxy-2-hydroxypropyl) ether of tetrachloro-bisphenol-A, di-(2-methacryloxyethyl) ether of tetrachloro-bisphenol-A, di-(3-methacryloxy-2-hydroxypropyl) ether of tetrabromo-bisphenol-A, di-(2-methacryloxyethyl) ether of tetrabromo-bisphenol-A, di-(3-methacryloxy-2-hydroxypropyl) ether of 1,4-butanediol, di-(3-methacryloxy-2-hydroxypropyl) ether of diphenolic acid, triethylene glycol dimethacrylate, polyoxypropyltrimethylol propane triacrylate, ethylene glycol dimethacrylate, butylene glycol dimethacrylate, 1,3-propanediol dimethacrylate, 1,2,4-butanetriol trimethacrylate, 2,2,4-trimethyl-1,3-pentanediol dimethacrylate, pentaerythritol trimethacrylate, 1-phenyl ethylene-1,2-dimethacrylate, pentaerythritol tetramethacrylate, trimethylol propane trimethacrylate, 1,5-pentanediol dimethacrylate, diallyl fumarate, styrene,1,4-benzenediol dimethacrylate, 1,4-diisopropenyl benzene, and 1,3,5-triisopropenyl benzene.

In addition to the monomers mentioned above, the photoresist material can also contain one or more free radical-initiated and polymerizable species with molecular weight of at least about 300. Monomers of this type are an alkylene or a polyalkylene glycol diacrylate and those described in U.S. Pat. No. 2,927,022.

Free radical initiators which can be activated by actinic radiation which are thermally inactive at and below 185 degrees Centigrade include the substituted or unsubstituted polynuclear quinones listed in the following: 9,10-anthraquinone, 1-chloroanthraquinone, 2-chloroanthraquinone, 2-methylanthraquinone, 2-tert-butylanthraquinone, octamethylanthraquinone, 1,4-naphthoquinone, 9,10-phenanthrequinone, 1,2-benzanthraquinone, 2,3-benzanthraquinone, 2-methyl-1,4-naphthone, 2,3-dichloronaphthoquinone, 1,4-dimethylanthraquinone, 2,3-dimethylanthraquinone, 2-phenylanthraquinone, 2,3-diphenylanthraquinone, 2,3-diphenylanthraquinone, sodium salt of anthraquinone alpha-sulfonic acid, 3-chloro-2-methylanthraquinone, retenequinone, 7,8,9,10-tetrahydronaphthacenequinone, and 1,2,3,4-tetrahydrobenz(a)anthracene-7,12-dione.

Other useful photoinitiators, of which some may be thermally active at temperatures lower than 85 degrees C, are described in U.S. Pat. No. 2,760,863.

Dyes of a photoreducible nature and other reducing agents are described in U.S. Pat. Nos. 2,850,445; 2,875,047; 3,097,096; 3,074,974; 3,097,097; and 3,145,104 as well as dyes of the phenazine, oxazine and quinone classes; Micheler's ketone, benzophenone, 2,4,5-triphenylimidazolyl dimers with hydrogen donors, and mixtures thereof as described in U.S. Pat. Nos. 3,427,161; 3,479185 and 3,549,367 can be used as initiators. The cyclohexadienone compounds of U.S. Pat. No. 4,341,860 are also useful as initiators. In addition, sensitizers described in U.S. Pat. No. 4,162,162 in combination with photoinitiators and photoinhibitors are useful.

Polymeric binders which can be used alone, or in combination with polymerizable monomers include the following: polyacrylate and alpha-alkyl polyacrylate esters, i.e. polymethyl methacrylate and polyethyl methacrylate; polyvinyl esters: i.e. polyvinyl acetate, polyvinyl acetate/acrylate, polyvinyl acetate/methacrylate and hydrolyzed polyvinyl acetate; ethylene/vinyl acetate copolymers; polystyrene polymers and copolymers, i.e. with maleic anhydride and esters; vinylidene chloride copolymers, i.e. vinylidene chloride/acrylonitrile; vinylidene chloride/methacrylate and vinylidene chloride/vinyl acetate copolymers; polyvinyl chloride and copolymers, i.e. polyvinyl chloride/acetate; saturated and unsaturated polyurethanes; synthetic rubbers, i.e. butadiene/acrylonitrile, acrylonitrile/butadiene/styrene, methacrylate/acrylonitrile/butadiene/styrene copolymers, 2-chlorobutadiene-1,3 polymers, chlorinated rubber, and styrene/butadiene/styrene, styrene/isoprene/styrene block copolymers; high molecular weight polyethylene oxides of polyglycols having average molecular weight from about 4,000 to 1,000,000; epoxides, i.e. containing acrylate or methacrylate groups; copolyesters; nylons or polyamides, i.e. N-methoxymethyl, polyhexamethylene adipamide; cellulose esters, i.e. cellulose acetate succinate and cellulose acetate butyrate; cellulose ethers, i.e. methyl cellulose, ethyl cellulose and benzyl cellulose; polycarbonates; polyvinyl acetal, i.e. polyvinyl butyral, polyvinyl formal; polyformaldehydes.

In addition to the polymeric binders listed above, particulate thickeners such as described in U.S. Pat. No. 3,754,920 i.e. silicas, clays, alumina, bentonites, kaolnites, and the like can be used.

Where aqueous developing of the photoresist is desirable the binder should contain sufficient acidic or other functionalities to render the composition processable in the aqueous developer. Suitable aqueous-processable binders include those described in U.S. Pat. No. 3,458,311 and in U.S. Pat. No. 4,273,856. Polymers derived from an aminoalkyl acrylate or methacrylate, acidic film-forming comonomer and an alkyl or hydroxyalkyl acrylate such as those described in U.S. Pat. No. 4,293,635 can be included.

Normally a thermal polymerization inhibitor will be present to increase the stability during storage of the photosensitive compositions. Such inhibitors are; p-methoxyphenol, hydroquinone, alkyl and aryl-substituted hydroqinones and quinones, tert-butyl catechol, pyrogallol, copper resinate, naphthylamines, beta-napthol, cuprous chloride, 2,6-di-tert-butyl-p-cresol, phenothiazine, pyridine, nitrobenzene and dinitrobenzene, p-toluequinone and chloranil. Also useful for thermal polymerization inhibitors are the nitroso compositions described in U.S. Pat. No. 4,168,982.

Dyes and pigments may also be added to increase the visibility of the resist image. Any colorant used however, should be transparent to the actinic radiation used.

An example of such photosensitive compositions is described in Table I of U.S. Pat. No. 4,693,959.

In the preparation of these formulations generally inert solvents are employed which are volatile at ordinary pressures. Examples include alcohols and ether alcohols, esters, aromatics, ketones, chlorinated hydrocarbons, aliphatic hydrocarbons, miscellaneous solvents such as dimethylsulfoxide, pyridine, tetrahydrofuran, dioxane, dicyanocyclobutane and 1-methyl-2-oxo-hexamethyleneimine, and mixtures of these solvents in various proportions as may be required to attain solutions. Antiblocking agents to prevent the coatings from adhering to the supporting films can also be included.

With some polymers, it is desirable to add a plasticizer, either solid or liquid, to give flexibility to the film or coating. Suitable plasticizers are described in U.S. Pat. No. 3,658,543. A preferred liquid plasticizer is nolylphenoxypoly(ethyleneoxy)-ethanol. A preferred solid plasticizer is N-ethyl-p-toluenesulfonamide.

Photoimageable compositions are also utilized as solder masks. In such application a photoimageable composition is used by applying the composition to printed circuit board and followed by photolithographic techniques to expose various underlying features on the board while masking others. During the soldering process the solder will deposit onto the exposed underlying components. It is necessary that the solder mask material be formulated such that it can be applied by the appropriate methods, for example curtain coating. Suitable photoimageable compositions including many that use epoxies are described in the following U.S. Pat. Nos. 4,279,985; 4,458,890; 4,351,708; 4,138,255; 4,069,055; 4,250,053; 4,058,401; 4,659,649; 4,544,623; 4,684,671; 4,624,912; 4,175,963; 4,081,276; 4,693,961; and 4,442,197.

More recently an improved cationically photoimageable solder mask is described in U.S. Pat. No. 5,026,624 assigned to the assignee of the present application, disclosure of which is incorporated herein by reference. In fact U.S. Pat. No. 5,026,624 teaches an improved photoimageable cationically polymerizable epoxy based coating material.

In processing negative working resists, unexposed areas of the imaged film are typically removed from the surface of a printed circuit board or substrate by action of a liquid developer in a spray form for a duration of several minutes or less. Depending on the particular type of photoresist composition the liquid developer may be a simple organic solvent, an aqueous solution of an inorganic base, or as described in U.S. Pat. No. 3,475,171, a combination of organic solvent and aqueous base to form a semi-aqueous developer.

Methyl chloroform (MCF, 1,1,1-trichloroethane), and methylene chloride (MC, dichloromethane) are solvents which are widely used in the electronic packaging art and in other arts for developing and removing a number of photoresists which are otherwise resistant to chemical attack.

The highly alkaline electroless copper plating baths used in additive processes provide a harsh environment for photoresist. In general, the more chemically impervious resists are removable in an organic solvent such as methylene chloride. For less demanding chemical environments, aqueous developable photoresists may be adequate. The organically developable resists, however, continue to be used in an electroless copper environment and in the print band and thin film technologies in conjunction with acrylate-based resist such as DuPont's Riston T-168 and solvent processed solder masks such as the DuPont Vacrel 700 and 900 series, environments in which the aqueous resists are vulnerable.

The use of 1,1,1-trichloroethane and methylene chloride is disfavored because of growing environmental concerns over the effect of gaseous halogenated hydrocarbons on the depletion of earth's ozone layer and concerns over introducing suspected carcinogens to the atmosphere. Several countries have set goals for their total elimination. However, there continue to be many manufacturing processes in which use of resists which are aqueously developable simply is not feasible.

The industry therefore continues the search for organic solvents as alternates to 1,1,1-trichloroethane and methylene chloride. The new solvents must meet specific manufacturing and environmental requirements with respect to flammability, toxicity, ability to effect dissolution, shelf-life, waste disposal, ability to recycle, simplicity of composition, and compatibility with a spectrum of resists.

Alternative solvents for stripping solvent based Riston photoresists are also described in Research Disclosures, June 1989 p. 302, published anonymously.

There have been previous attempts reported in the art to provide environmentally friendly alternatives to 1,1,1-trichloroethane and methylene chloride. However, none of the references describe the simple, environmentally acceptable, room temperature developers and strippers described by the commonly assigned, copending U.S. application Ser. No. 07/781,542, filed Oct. 22, 1991, of N. R. Bantu, Anilkumar Bhatt, Ashwinkumar Bhatt, G. W. Jones, J. A. Kotylo, R. J. Owen, K. I. Papathomas, and A. K. Vardya for *Photoresist Develop And Strip Solvents and Methods for their Use*. This application describes the use of 4-methyl-1,2- dioxolan-2-one (propylene carbonate, methyl ethylene carbonate, 1,2-propylene carbonate) as a developer and as a stripping agent. This material has the structure:

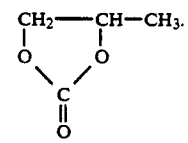

Bantu et al describe its use as an alternative to halogenated hydrocarbon developers and strippers for use in developing and stripping acrylate based photoresist such as Riston T-168 and polymethyl methacrylate, and solvent processed solder masks such as the Vacrel 700 and 900 series.

U.S. application Ser. No. 07/781,542 describe developing the radiation-exposed resist in a high boiling solvent selected from the group consisting of propylene carbonate (PC), gamma butyrolactone (BLO) and benzyl alcohol (BA). The process occurs at about 24 to 45 degrees Centigrade for about 0.5–12 minutes and is normally followed by a warm water or alternate low boiling solvents rinse to remove excess developer.

The aforementioned solvents of U.S. application Serial No. 07/781,542 are high boiling solvents, while the common developers of the prior art for developing Riston type photoresists are low boiling solvents. The use of low boiling solvents such as methyl chloroform (MCF), methyl ethyl ketone (MEK), xylenes or mixtures thereof are similar to the methylene chloride stripping process.

By way of contrast high boiling solvents, i.e. n-methyl pyrolidone (NMP), gamma-butyrolactone (BLO), dimethyl sulfoxide (DMSO) and propylene carbonate (PC) must be followed by a rinsing step with compatible solvent or water. Furthermore, in order to obtain dissolution times comparable to those of MC, it is necessary that the temperature during stripping be maintained between 50 degrees Centigrade and 100 degrees Centigrade and conditions. Moreover, brushing is necessary during stripping for product quality and high throughput. However, the combination of brushing with these relatively high temperatures results in the removal of a photoresist product containing solubilized and solid photoresist polymer, as well as monomers, additives, initiators, surfactants, dyes and other components, hereinafter collectively referred to as "photoresist products" and "photoresist solids".

Thus, there is a clear need for a low cost process for the separation and recovery of cyclic alkylene carbonate solvents, as propylene carbonate, from the photoresist materials for recycle and reuse.

OBJECTS OF THE INVENTION

It is a primary object of the invention to provide a simple, low cost process to recycle and reuse cyclic alkylene carbonates, as propylene carbonate.

It is a further object of the invention to recycle and reuse cyclic alkylene carbonate. for example, propylene carbonate, from the waste stream of a photolithographic process with minimal hydrolysis of the cyclic alkylene carbonate, to the corresponding glycol, for example, propylene carbonate and its homologs to propylene glycol and its homologs.

It is a still further object of the invention to recover the carbonate at conditions of temperature and pressure which minimize the hazards of combustion and explosion, averting the need for special construction.

SUMMARY OF THE INVENTION

The present invention recovers the non-toxic solvents of the type described by U.S. application Ser. No. 07/781,542. The solvents of U.S. application Ser. No. 07/781,542 are high boiling solvents. By way of contrast, the common developers of the prior art for developing Riston type photoresists are low boiling solvents.

Developing and stripping of organic polymeric films with the high boiling solvents of U.S. Application Serial No. 07/781,542, i.e. n-methyl pyrolidone (NMP), gamma-butyrolactone (BLO), dimethyl sulfoxide (DMSO) and propylene carbonate (PC) requires a subsequent rinsing step with a compatible solvent or water. This introduces a complication into the recovery of the cyclic alkylene carbonate solvent, the contamination thereof by the solvent or water introduced during the rinsing step.

Furthermore, in order to obtain polymer dissolution times comparable to those of halogenated solvents, it is necessary that temperature during stripping be maintained at above about 50 degrees Centigrade, and generally between about 50 degrees Centigrade and 100 degrees Centigrade. This introduces a still further complication into the recovery of the cyclic alkylene carbonate solvent, the degradation or decomposition thereof and the formation of degradation or decomposition products.

However, these problems are solved by the method of recovering propylene carbonate described herein. According to the process described herein, propylene carbonate is recovered from an effluent stream of a process in which the propylene carbonate was used to remove photoresist materials, including organic polymeric materials from a substrate.

The effluent stream contains cyclic alkylene carbonate, for example, propylene carbonate, the glycol hydrolysis product thereof, e.g., propylene glycol, water, and photoresist products, such as dissolved polymer, polymeric solids, monomer, surfactant, dyes, photoinitiators and fragments thereof, and the like. In the recovery process the propylene carbonate effluent is fed to a first separation stage, such as a vertical tube heat exchanger type evaporator, and separated into (i) water and volatiles, and (ii) propylene carbonate. This lowers the concentration of water in the propylene carbonate to a level that is low enough to substantially avoid further hydrolysis of propylene carbonate to propylene glycol.

The dewatered propylene carbonate is then separated, for example in a wiped film type evaporator, to separate the propylene carbonate from high boiling photoresist materials and polymeric solids. In this stage the dewatered propylene carbonate is separated into (i) a propylene carbonate fraction, and (ii) a photoresist materials fraction. The photoresist materials contains photoresist material in propylene carbonate.

The propylene carbonate fraction is further separated in a fractionation means into a higher vapor pressure propylene glycol fraction, and a lower vapor pressure propylene carbonate fraction.

THE FIGURES

The invention may be understood by reference to the FIGURES appended hereto.

DETAILED DESCRIPTION OF THE INVENTION

Figure 1:
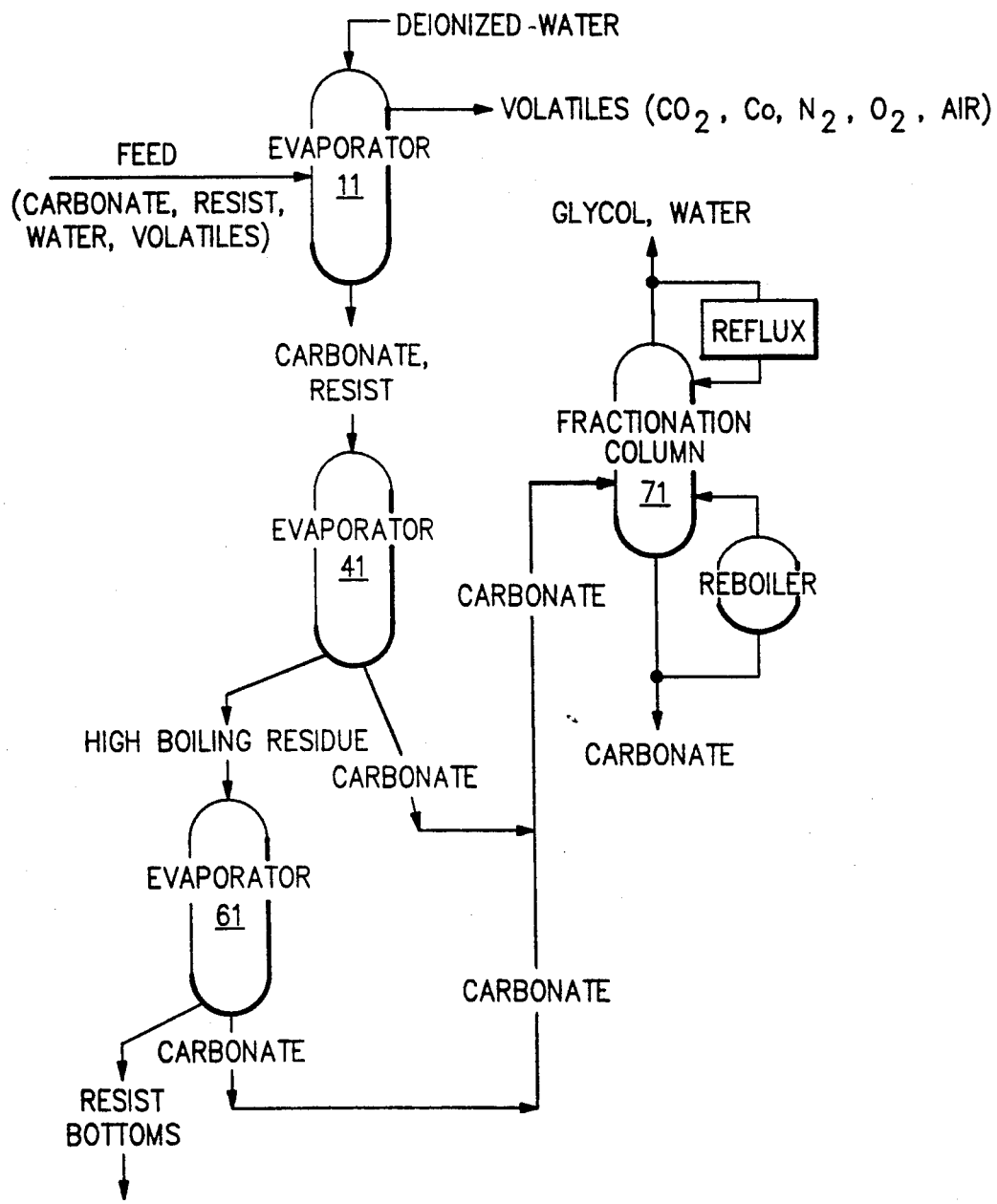
FIGS. 1 and 1A are flow charts of alternative exemplifications of the cyclic alkylene carbonate recovery process of the invention.

Impure propylene carbonate is an effluent from an upstream industrial process in which relatively pure propylene carbonate is used as either a developer or a stripper, or as both, in the removal of a thin film, layer, or coating of a photoresist material. The impure propylene carbonate contains both solubilized polymer and dispersed solid polymer. In one embodiment of the invention the polymer is a photoresist, for example, a negative photoresist formed of acrylic acid and acrylate ester moieties, such as Dupont Riston, and the effluent is the effluent of either or both of the developing and stripping steps. The removed photoresist material, including polymer, whether solubilized or dispersed, along with monomer, solvents, surfactants, initiator, initiator fragments, dyes, and the included, are referred collectively to herein as "photoresist materials" and as "solids."

While the invention is described and illustrated with respect to propylene carbonate,

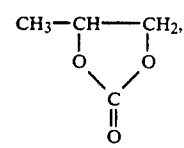

it is, of course, to be understood, that higher cyclic alkylene carbonate homologs of propylene carbonate, such as

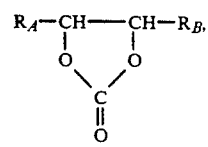

where $R_A$ and $R_B$ are short chain alkyl groups, may be used. Exemplary short chain alkyl groups are $CH_3-(CH_2)_n-$, where n in $R_A$ and $R_B$ are independent integers from 0 to 3. It is, of course, further to be understood, that the vapor pressure of the cyclic alkylene carbonate must be high enough to allow fractionation or separation.

In the embodiment of the invention where the polymer is an acrylic-acrylate type photoresist and the solvent is propylene carbonate, the effluent of the photolithographic process contains (i) above about 50 weight percent propylene carbonate, and generally from about 96 weight percent to about 99 weight percent of propylene carbonate, (ii) up to about 40 weight percent photoresist materials, and generally from about 0.2 weight percent to about 1.0 weight percent of "photoresist materials," i.e., "solids," that is, both dispersed solid polymer and dissolved, solubilized polymer, (iii) up to about 5 weight percent, and generally from about 0.1 weight percent to about 0.5 weight percent of propylene glycol, a hydrolysis decomposition product of propylene carbonate, and (iv) up to about 5 weight percent, and generally from about 0.1 weight percent to about 2.5 weight percent of water. These weight percentages should total 100 weight percent, but may total less than 100 weight percent if other impurities are present.

In order to recycle the cyclic alkylene carbonate, e.g., propylene carbonate, for reuse as a developing agent or stripping agent, it is necessary to recover a purified cyclic alkylene carbonate, e.g., propylene carbonate. By purified propylene carbonate is generally meant a propylene carbonate product that is substantially free of solids, i.e., less than 0.1 percent water, and preferably less than 0.050 weight percent water, and less than 0.05 weight percent propylene glycol as evidenced by a color value of less than 20 APHA (reference to platinum-cobalt standard).

FIG. 1 is a flow chart for recovering propylene carbonate from an effluent stream of a process in which propylene carbonate removes an organic photoresist material from a substrate. This effluent stream is an aqueous propylene carbonate effluent of propylene carbonate, water, and photoresist materials solids stream.

Figures 2, 4:
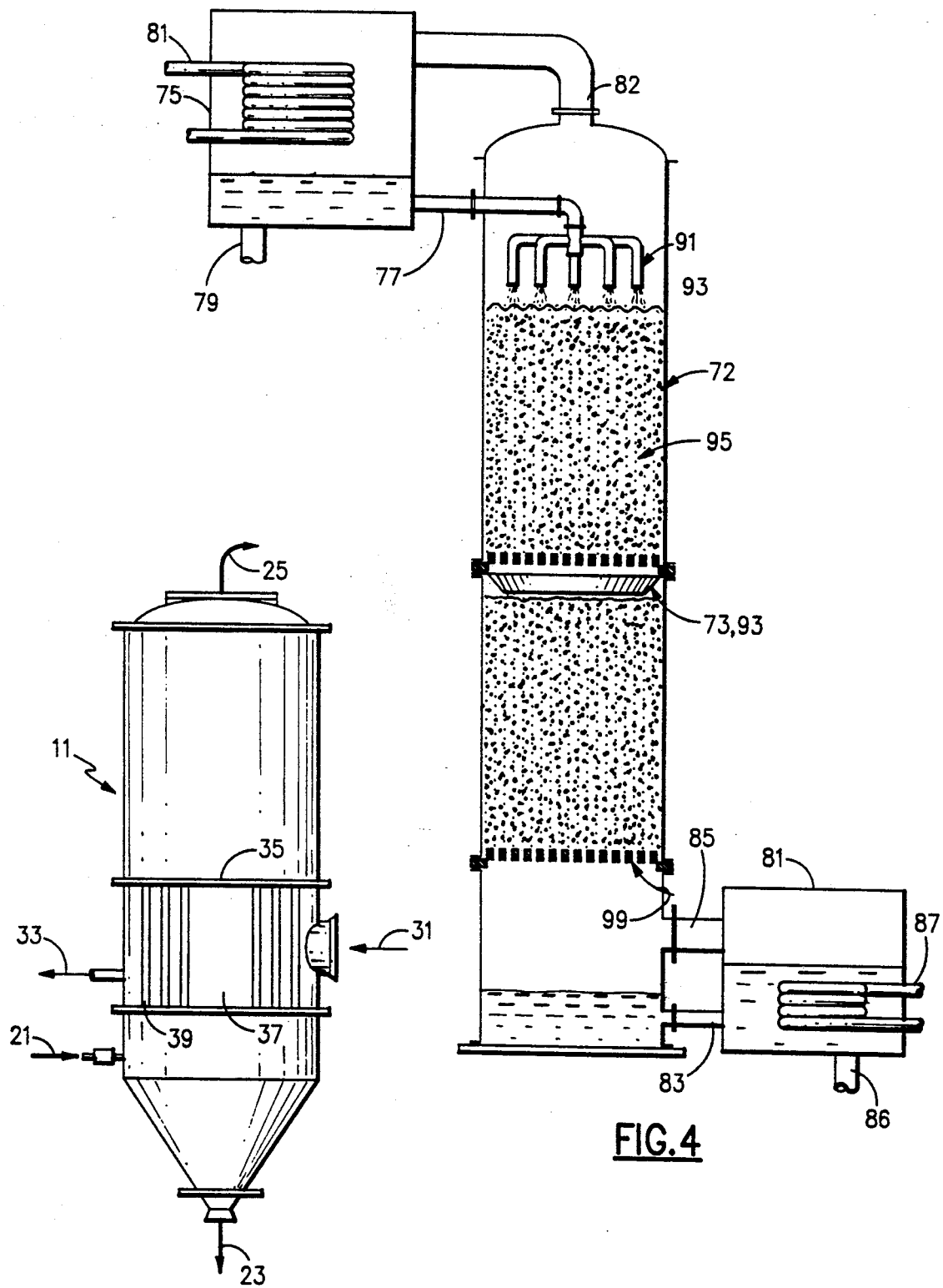
FIG. 2 is a cutaway view of a single stage, vertical tube heat exchanger type evaporator useful in the initial separation of the cyclic alkylene carbonate, e.g., propylene carbonate, from water and the volatiles.
FIG. 4 is a cutaway view of a packed tower distillation column useful in the separation of the cyclic alkylene carbonate, e.g., propylene carbonate, recycle from the alkylene glycol contaminant, e.g., propylene glycol contaminant.

In the recovery process illustrated in FIG. 1 the effluent, e.g., propylene carbonate effluent, is fed to a dewatering unit, which is the first separation stage 11. This may be a short tube, vertical pipe heat exchanger type evaporator, as shown in FIG. 2. In the first separation stage the effluent stream is separated into two streams, (i) a gaseous stream of water and volatiles withdrawn at the top of the first separation stage 11, and (ii) a liquid propylene carbonate stream.

This first stage separation lowers the concentration of water in the cyclic alkylene carbonate to a level that is low enough to substantially avoid hydrolysis of the carbonate to the corresponding glycol. In the case of propylene carbonate, the propylene carbonate concentration is reduced to a level that is low enough to substantially avoid hydrolysis of propylene carbonate to propylene glycol. In the first stage separator, as heat exchanger type evaporator 11, the total pressure in the heat exchanger is maintained higher than the vapor pressure of propylene carbonate at its open cup flash point. For a process stream containing 0.1 weight percent water in propylene carbonate, this corresponds to maintaining the process stream temperature below the open cup flash point of the propylene carbonate. That is, the process stream is maintained below about 132 degrees C, and the total pressure is preferably maintained below about 25 torr.

The bottom product of the first separation stage is dewatered propylene carbonate, preferably containing (i) from about 96 weight percent to about 99 weight percent of propylene carbonate, (ii) from about 0.2 weight percent to about 0.5 weight percent of "solids," that is, both dispersed solid polymer and dissolved, solubilized polymer, (iii) from about 0.1 weight percent to about 0.5 weight percent of propylene glycol, and (iv) from about 0.08 weight percent to about 0.10 weight percent of water.

The dewatered propylene carbonate from the first stage separation 11 is further separated in a second stage separation 41 to separate the propylene carbonate from high boiling materials and polymeric solids, for example, by evaporation. In the second stage separation, which may be carried out in a wiped film evaporator, 41, of the type shown in FIG. 3, the dewatered propylene carbonate is separated into (i) a propylene carbonate fraction, and (ii) a photoresist materials solids fraction. The photoresist solids fraction contains photoresist materials such as polymeric materials, in propylene carbonate.

The pressure in the evaporator 41 is maintained below about 25 torr, for example at about 5 to about 15 torr. The temperature in the evaporator 41 is maintained above about 120 degrees Centigrade.

The second stage separation 41 yields an overhead product of about 98 to about 99 weight percent propylene carbonate and a bottom product of photoresist material in propylene carbonate.

The overhead product of the second stage separation 41, that is the evaporated, dewatered propylene carbonate, is fed to a fractionation means 71. This fractionation means, which may be a packed tower 71 of the type shown in FIG. 4, is used to further separate the evaporated, dewatered propylene carbonate into a higher vapor pressure propylene glycol fraction and a lower vapor pressure propylene carbonate fraction.

Optionally, propylene carbonate may also be recovered from the bottom product of the second stage, 41. The bottom product is photoresist material in the cyclic alkylene carbonate solvent, e.g., in propylene carbonate. The bottom product contains from about 90 to about 98 propylene carbonate, balance solids.

Figure 1A:
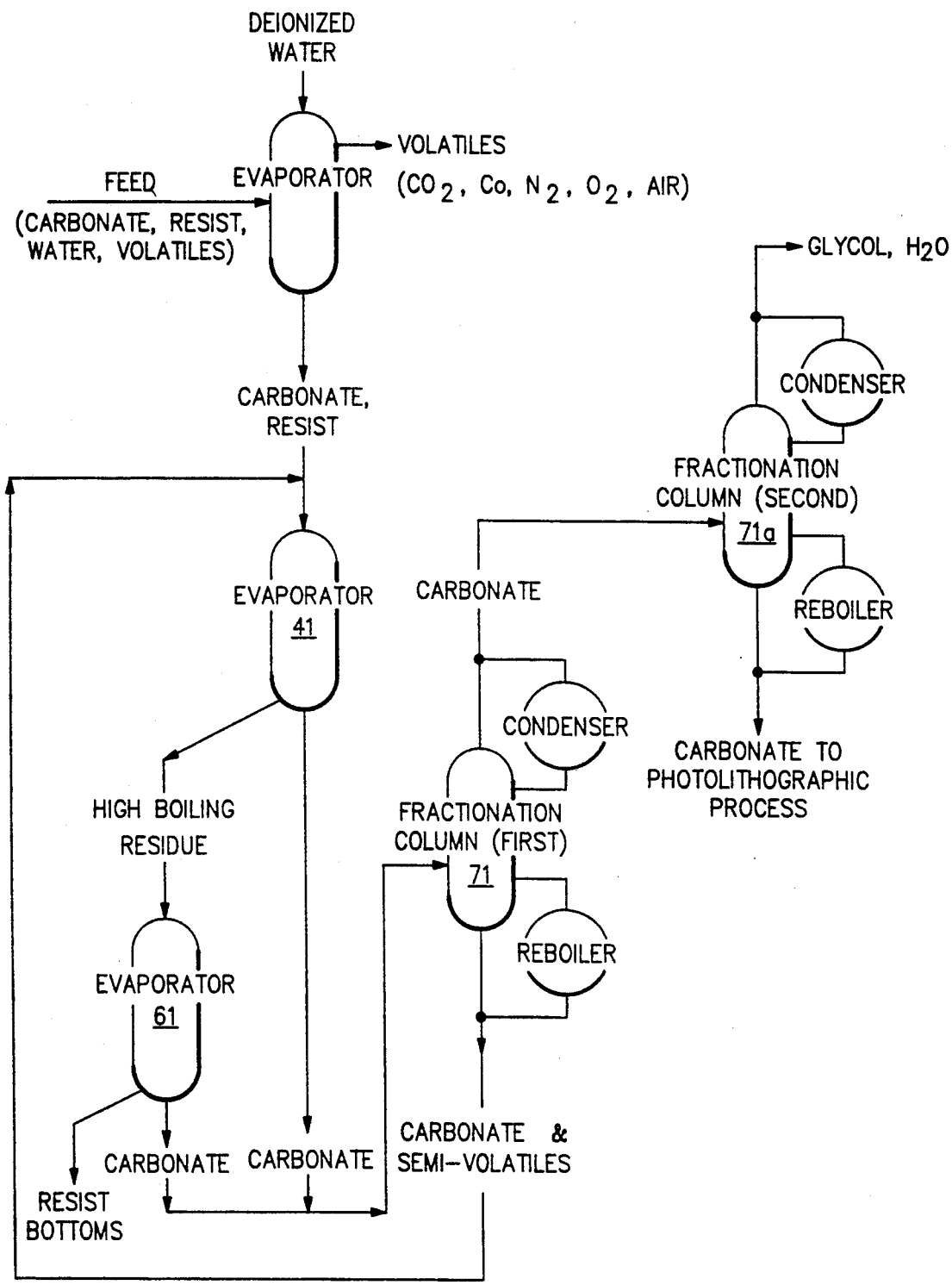

According to a further alternative method of the invention, the bottom product of the evaporator 41 is fed to a further evaporation step 61 and thereafter to fractionating means 71-71a. The overhead product of the second evaporator goes to fractionating unit 71-71a, as shown in FIG. 1A. The bottom product of the evaporator unit 61 is a polymer rich material that is discharged.

The product of the fractionation step, 71, is a fractionated product that is substantially free of polymeric materials. By being substantially free of polymeric materials is meant that the propylene carbonate product has a color value less than 20 APHA (reference to platinum-cobalt standard). The fractionated product is also substantially free of water, containing less than 0.050 weight percent water.

To recover a bottom product in the evaporator or pot of high purity cyclic alkylene carbonate, for example, high purity propylene carbonate, without degradation of the carbonate the column pressure must be carefully maintained. Preferably the top pressure of the fractionation means is less than 15 torr, and generally from about 6 to about 10 torr, and the bottom pressure is less then about 35 torr and generally is about 20 torr.

Critical to a high recovery of high purity cyclical alkylene carbonate, e.g., propylene carbonate, is the minimal in-process loss of cyclical alkylene carbonate. Propylene carbonate is not just lost with the solids. It is also lost chemically, for example, through the formation of by-products, such as hydrolysis products.

We have found that control of these in-process loss pathways requires log operating temperatures, minimal times at higher temperatures, and the substantial absence of water. The operating temperature and the exposure time to heat input surfaces are held to a minimum to slow the rate of decomposition of the cyclic alkylene carbonate solvent, for example, propylene carbonate.

Low temperature and low exposure times to heat transfer surfaces both necessitate processing under substantial vacuum conditions. Substantial vacuum conditions reduce and even eliminate the need to heat the cyclic alkylene carbonate streams, for example, propylene carbonate streams, to high temperatures. An upper temperature that appears to avoid adverse by-products is 160 degrees Centigrade. A convenient design and operating temperature limit is the open cup flash point of the cyclic alkylene carbonate. For propylene carbonate the open cup flash point is 132 degrees Centigrade. In the case of propylene carbonate, processing below the 132 degree Centigrade open cup flash point makes it possible to minimize combustion and explosion concerns. This mitigates the need for damage limiting construction, as well as flame proof and explosion proof recovery equipment. Additionally, low temperatures reduce the rate of decomposition.

In another embodiment a nitrogen blanket may be used. The nitrogen blanket reduces combustion potential and provides a higher quality product.

Moreover, if water is removed early in the process sequence it is possible to minimize decomposition of the cyclic alkylene carbonate, such as propylene carbonate, for example by hydrolysis. These considerations drive the process sequence shown in FIG. 1 and in the individual process steps shown below.

Turning now to the individual process steps, the first step of the process is the removal of water. This is shown in FIG. 2 as being carried out in a short tube vertical heat exchanger type evaporator 11, such as a falling film type evaporator. The short tube vertical heat exchanger type evaporator 11 has a feed stream 21, which is separated in the evaporator 11 into a bottom or liquid stream 23 and an overhead or gas stream 23. Additionally, water, for example, deionized water, may be fed to the top of the evaporator. Heat transferred to this water from the alkylene carbonate vapor aids in condensing the alkylene carbonate vapor, and thereby reduces the loss of alkylene carbonate with the overhead 23.

Steam enters the heat exchanger type evaporator 11 through steam inlet 31, which is the inlet to a shell and tube type heat exchanger 31. The steam is the shell side medium. In one exemplification the tubes 39 are vapor risers concentrically arrayed around an optional downcomer 37. However, the downcomer is not a necessary part of the evaporator.

Evaporating feed rises through the tubes or vapor risers 39, and condensate returns, for example, through downcomer 37, when present. Steam exits the shell and tube heat exchanger 31 through outlet 33.

The incoming stream 21 enters the vertical heat exchanger type evaporator 11. The pressure within the evaporator 11 is maintained at about 20-25 Torr. The temperature of the feed is raised to about 120° C., flashing water and other volatile species and gases from the liquid stream.

Figure 3:
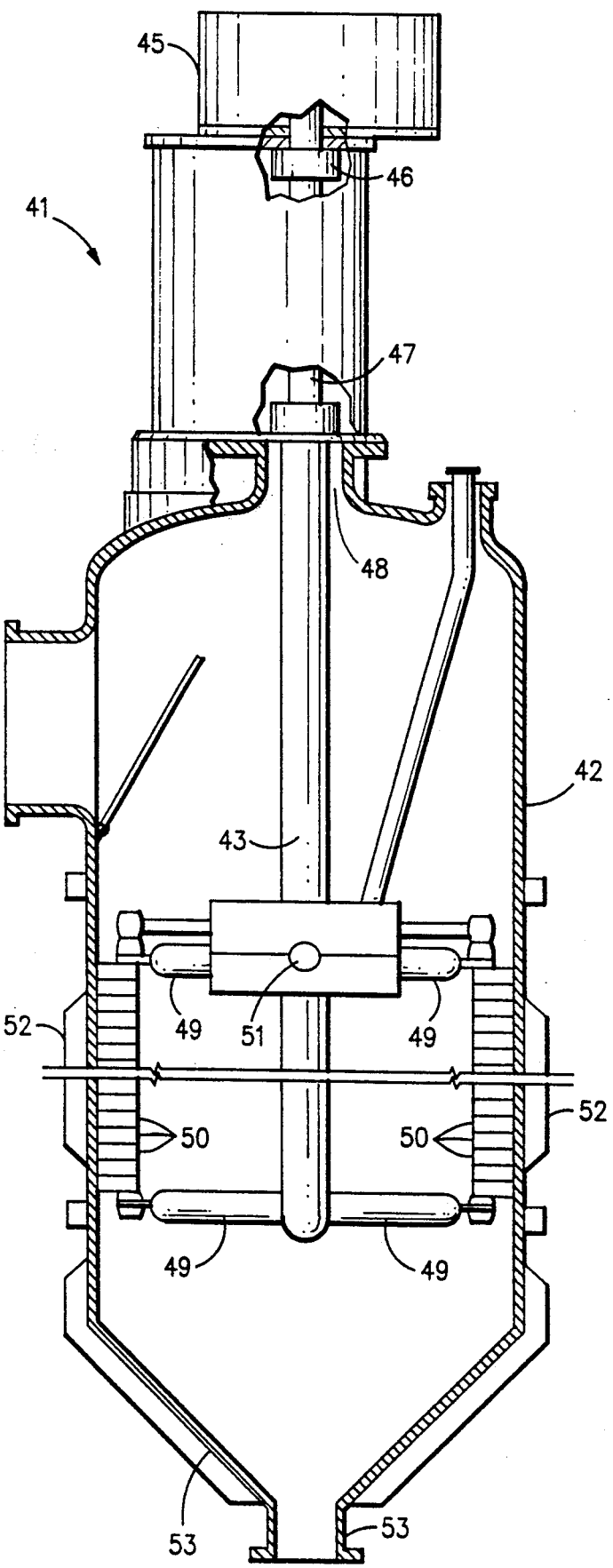
FIG. 3 is a cutaway view of a wiped film evaporator useful in the separation of the cyclic alkylene carbonate, e.g., propylene carbonate, from the solids.

The liquid product 23 of the first stage separation 11 is the feed to the second stage separation 41. The second stage separator 41 is illustrated in FIG. 3 as a single effect wiped film evaporator.

The pressure within the single effect wiped film evaporator 41 is maintained at 6 to 15 Torr, and the feed stream is heated to maintain a temperature of about 90 degrees Centigrade to about 120 degrees Centigrade. The propylene carbonate vaporizes, is condensed to a liquid and is removed. The remaining residue stream contains the low vapor pressure, high boiling temperature components, which may even be non-volatile, such as resist residues. The resist residues are in the propylene carbonate.

Wiped film evaporators, such as wiped film evaporator 41, are described generally in, for example U.S. Pat. No. 4,173,246 to Erwin J. Nunlist and James Mitchell for *Feed Distributor For Glassed Steel Wiped Film Evaporator*.

A wiped film evaporator 41 has a cylindrical vessel, 42, as a steel vessel. The interior walls of the vessel may be metal, as stainless steel, super alloys, and the like. Alternatively, the interior walls may be lined, for example, with glass or an enamel. By an enamel is meant a porcelain enamel. Porcelain enamels are vitreous or partially devitrified inorganic materials. The glass or enamel lining is bonded to the steel vessel 42.

Wiped film evaporators 41 are characterized by a rotating wiper assembly 43 extending along the vertical axis of the evaporator 41. The rotating wiper assembly 43 includes a rotating shaft 44, arms 49 extending outwardly from the rotating shaft 44, and blades 50 at the ends of the arms 49 for spreading the propylene carbonate onto the interior wall of the vessel 42.

The rotating shaft 44 is driven by a motor 45, through bearings 46, and coupling 47, extending through a seal 48 in the top of the vessel.

The walls of the wiped film evaporator 41 are heated by steam in steam jackets 52.

In operation the propylene carbonate product 23' of the first stage evaporator 11 is introduced into the wiped film evaporator 41 through opening 23". The liquid feed is led to a distributor 51. Centrifugal force and gravity drive the propylene carbonate out of the distributor 51 to the blades 50 at the ends of the arms 49. The blades 50 spread the cyclic alkylene carbonate, such as propylene carbonate, onto the interior surface of the vessel 42, where the steam in the steam jacket 52 heats the cyclic alkylene carbonate, e.g., propylene carbonate, giving off vapor products. The liquid residues fall to a conical collecting region 53 and outlet 54.

The liquid product of the second stage separation 41 may be further processed, for example through use of a downstream evaporator 61, to concentrate the resist solids and increase solvent distillate yield. The final residue of the downstream evaporator 61 becomes a principal waste of the process.

Vapors from units 41 and 61, being cyclical alkylene carbonate substantially free of photoresist materials, along with minor amounts of other volatiles, enter the fractionation column 71. In the fractionation column 71 components that are less volatile than the cyclic alkylene carbonate, e.g., resist, are condensed from the vapor phase. This condensation is effected by a reflux stream introduced at the top of the column 71. A liquid stream leaves the bottom of column 71. This stream may be removed from the system, or it may be re-introduced at an earlier stage. The overhead of the column is a purified, fractionated cyclic alkylene carbonate stream.

The overhead products of the second stage separator 41, and the downstream evaporator 61, if any, are introduced to a vertical packed column 71. Details of the column 71 are shown in FIG. 4.

A packed tower distillation column 71 is shown in FIG. 4. Structurally, the packed tower 71 includes a shell or body 72, with a condenser 75 at the top and a reboiler 81 at the bottom. Feed is introduced into the tower 71 through liquid feed means 73, to a liquid distributor 91, and a packing restrainer 93. The liquid distributor 91 and the packing restrainer 93 distribute the feed (73) and the condenser return 77 onto and through the packing 95 and, optionally a liquid redistributor or redistributors 97.

Upward flowing gas, for example, return 85 from the reboiler 81, contacts the downward flowing liquid, providing a low boiling, high vapor top product 82 at the condenser 75, which is condensed by a condenser 75 heat exchanger 81 and recovered as a high vapor pressure, low boiling temperature liquid 79, and a high boiling, low vapor pressure product 83 at the reboiler 81., which is recovered as a liquid product 86. The remaining reboiler liquid is vaporized by heat exchanger 87.

The operating pressure within the column 71 varies from 6 to 10 Torr at the top to 15–20 Torr at the bottom. Fractionation occurs within this unit, with more volatile fractions, such as by-product propylene glycol, travelling to the top of column 71 to be condensed and the less volatile propylene carbonate circulating within the bottom of the column 71 as a liquid at its boiling point. Normal methods of distillation column operation, including control of overhead reflux ratio and of bottom reboil ratio, are applied.

Propylene carbonate product, suitable for re-use in manufacturing, is discharged from the bottom of the fractionation column 71.

The multi-stage separation process described herein starts with a heavily contaminated feed, with visible suspended solids, strong color, and opaqueness. This feed is processed to yield water-white (clear) product, free of suspended solids and having a color value of less than 20 APHA (referenced to platinum-cobalt standard). The method of the invention is also particularly effective in water removal, reducing the water content from 1.6 weight percent in the feed to 0.030 weight percent in the recovered propylene carbonate product.

While the invention has been described with respect to certain preferred embodiments and exemplifications, it is not intended to limit the scope of the invention thereby, but solely by the claims appended hereto.

We claim:

1. A method of recovering propylene carbonate from an effluent stream of a process in which propylene carbonate removes an organic polymeric material from a substrate and thereby forms a propylene carbonate effluent, said method comprising the steps of:
   a. feeding the propylene carbonate effluent to a separation means and separating water and volatiles from the propylene carbonate;
   b. recovering the dewatered propylene carbonate and thereafter evaporating the dewatered propylene carbonate to separate the propylene carbonate from high boiling materials and photoresist materials, and recovering therefrom a propylene carbonate fraction.

2. The method of claim 1 comprising further separating the evaporated, dewatered propylene carbonate into a high vapor pressure propylene glycol fraction and a low vapor pressure propylene carbonate fraction.

3. The method of claim 1 comprising transferring heat to the propylene carbonate stream and selectively volatizing water and volatiles therefrom.

4. The method of claim 3 comprising removing water to lower the concentration thereof low enough to substantially avoid hydrolysis of propylene carbonate to propylene glycol.

5. The method of claim 3 comprising maintaining the temperature in the separation means below the open cup flash point of the propylene carbonate.

6. The method of claim 5 comprising maintaining the pressure in the separation means below 132 degrees Centigrade.

7. The method of claim 3 comprising maintaining the temperature in the separation means below about 160 degrees Centigrade.

8. The method of claim 3 comprising maintaining the total pressure in the separation means below about 35 torr.

9. The method of claim 1 comprising recovering the dewatered propylene carbonate and thereafter evaporating the dewatered propylene carbonate to separate the propylene carbonate from contained photoresist materials.

10. The method of claim 9 comprising evaporating the dewatered propylene carbonate in an evaporator.

11. The method of claim 10 comprising maintaining the pressure in the evaporator at below about 25 torr.

12. The method of claim 9 comprising maintaining the temperature in the evaporator below about 120 degrees Centigrade.

13. The method of claim 9 comprising recovering an overhead product of propylene carbonate and a bottom product of photoresist material in propylene carbonate.

14. The method of claim 1 comprising feeding the evaporated, dewatered propylene carbonate to a fractionation means, and further separating the evaporated, dewatered propylene carbonate into a high vapor pressure propylene glycol fraction and a low vapor pressure propylene carbonate fraction.

15. The method of claim 14 comprising recovering a fractionated product, substantially free of photoresist materials, having a color value less than 20 APHA (reference to platinum-cobalt standard).

16. The method of claim 14 comprising recovering a fractionated product, containing less than 0.030 weight percent water.

17. The method of claim 14 maintaining the top pressure of the fractionation means less than about 15 torr.

18. The method of claim 14 maintaining the bottom pressure of the fractionation means less than about 35 torr.

19. The method of claim 1 comprising recovering a bottom product of photoresist material in propylene carbonate from the evaporating means, and feeding the bottom product to a fractionating means to recover the propylene carbonate therefrom.

20. The method of claim 1 comprising recovering a propylene carbonate product containing less than 0.1 weight percent water.

21. A method of recovering propylene carbonate from an effluent stream of a process in which propylene carbonate removes an organic photoresist material from a substrate and thereby forms a propylene carbonate effluent, said method comprising the steps of:

a. feeding the propylene carbonate effluent to a heat exchanger, maintaining the pressure in the heat exchanger below the vapor pressure of propylene carbonate at its open cup flash point, and separating water and volatiles from the propylene carbonate to lower the concentration of water in the propylene carbonate low enough to substantially avoid hydrolysis of propylene carbonate to propylene glycol;

b. recovering the dewatered propylene carbonate and thereafter evaporating the dewatered propylene carbonate in an evaporator to separate the propylene carbonate from high boiling materials and polymeric solids, and recovering therefrom (i) a propylene carbonate fraction, and (ii) a polymeric solids fraction containing photoresist material in propylene carbonate; and c. further separating the evaporated, dewatered propylene carbonate in a fractionation means into a high vapor pressure propylene glycol fraction at a pressure below about 15 torr, and a low vapor pressure propylene carbonate fraction at a pressure below about 35 torr.

22. The method of claim 21 comprising maintaining the temperature in the heat exchanger below 160 degrees Centigrade.

23. The method of claim 21 comprising maintaining the pressure in the heat exchanger below about 35 torr.

24. The method of claim 21 comprising recovering the bottom product of photoresist material in propylene carbonate from the evaporating means of step b, and separating the bottom product to recover propylene carbonate therefrom.

25. The method of claim 21 comprising recovering a fractionated product, substantially free of photoresist materials, having a color value less than 20 APHA (reference to platinum-cobalt standard).

26. The method of claim 21 comprising recovering a fractionated product, substantially free of water.

27. A method of recovering a cyclic alkylene carbonate from an effluent stream of a process in which cyclic alkylene carbonate removes an organic photoresist material from a substrate and thereby forms an effluent of photoresist material and cyclic alkylene carbonate, said method comprising the steps of:

a. feeding the cyclic alkylene carbonate effluent to a separation means and separating water and volatiles from the cyclic alkylene carbonate;

b. recovering the dewatered cyclic alkylene carbonate and thereafter evaporating the dewatered cyclic alkylene carbonate to separate the cyclic alkylene carbonate from high boiling materials and polymeric solids, and recovering therefrom a cyclic alkylene carbonate fraction.

28. The method of claim 27 comprising further separating the evaporated, dewatered cyclic alkylene carbonate into a high vapor pressure cyclic alkylene glycol fraction and a low vapor pressure cyclic alkylene carbonate fraction.

29. The method of claim 27 wherein the cyclic alkyl carbonate has the structural formula

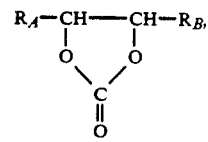

where $R_A$ and $R_B$ are independently chosen from the group consisting of H— and $CH_3$—$(CH_2)_n$—, where n is an integer from 0 to 3, and at least one of $R_A$ and $R_B$ is $CH_3$—$(CH_2)_n$—.

30. The method of claim 27 comprising transferring heat to the cyclic alkylene carbonate stream and selectively volatizing water and volatiles therefrom.

31. The method of claim 30 comprising removing water to lower the concentration thereof low enough to substantially avoid hydrolysis of cyclic alkylene carbonate to cyclic alkylene glycol.

32. The method of claim 30 comprising maintaining the temperature in the separation means below the open cup flash point of the cyclic alkylene carbonate.

33. The method of claim 32 wherein the cyclic alkylene carbonate is propylene carbonate, comprising maintaining the temperature in the separation means below 132 degrees Centigrade.

34. The method of claim 27 comprising maintaining the temperature in the separation means below 160 degrees Centigrade.

35. The method of claim 30 comprising maintaining the total pressure in the separation means below about 35 torr.

36. The method of claim 27 comprising recovering the dewatered cyclic alkylene carbonate and thereafter evaporating the dewatered cyclic alkylene carbonate to separate the cyclic alkylene carbonate from contained photoresist materials.

37. The method of claim 36 comprising evaporating the dewatered cyclic alkylene carbonate in an evaporator.

38. The method of claim 37 comprising maintaining the pressure in the evaporator at below about 15 torr.

39. The method of claim 36 comprising maintaining the temperature in the evaporator below about 120 degrees Centigrade.

40. The method of claim 36 comprising recovering an overhead product of cyclic alkylene carbonate and a bottom product of photoresist material in cyclic alkylene carbonate.

41. The method of claim 27 comprising feeding the evaporated, dewatered cyclic alkylene carbonate to a fractionation means, and further separating the evaporated, dewatered cyclic alkylene carbonate into a high vapor pressure cyclic alkylene glycol fraction and a low vapor pressure cyclic alkylene carbonate fraction.

42. The method of claim 41 comprising recovering a fractionated product, substantially free of photoresist materials, having a color value less than 20 APHA (reference to platinum-cobalt standard).

43. The method of claim 41 comprising recovering a fractionated product, containing less than 0.030 weight percent water.

44. The method of claim 36 comprising recovering a fractionated product, containing less than 0.10 weight percent water.

45. The method of claim 41 maintaining the top pressure of the fractionation means less than about 15 torr.

46. The method of claim 36 maintaining the bottom pressure of the fractionation means less than about 35 torr.

47. The method of claim 27 comprising recovering a bottom product of photoresist material in cyclic alkylene carbonate from the evaporating means, and feeding the bottom product to a fractionating means to recover the cyclic alkylene carbonate therefrom.

* * * * *